United States Patent [19]

Kashkina et al.

[11] 3,943,150
[45] Mar. 9, 1976

[54] SALT OF B-DIETHYLAMINOETHYL ESTER OF P-AMINOBENZOIC ACID WITH ACETAL OF POLYVINYL ALCOHOL AND GLYOXALIC AND METHOD OF PREPARING SAME

[76] Inventors: Nadezhda Alexandrovna Kashkina, ulitsa Talsu, 9/11, kv. 22; Milda Yanovna Pormale, ulitsa Suvorova, 104, kv. 10; Arvid Yanovich Kalnish, ulitsa Sverdlova, 8, kv. 3; Yan Alexandrovich Surna, ulitsa Maza Kaiju, 3, kv. 3, all of Riga, U.S.S.R.

[22] Filed: Apr. 26, 1974

[21] Appl. No.: 464,669

[52] U.S. Cl. ......... 260/340.7; 260/73 R; 260/78 A; 424/278
[51] Int. Cl.$^2$ ............... C07D 319/06; A01N 9/28
[58] Field of Search ............ 200/340.7, 73 R

[56] References Cited
UNITED STATES PATENTS
3,560,464  2/1971  Toyoshima et al. ............ 260/73 R

OTHER PUBLICATIONS
Richter, "Textbook of Organic Chemistry," John Wiley & Sons, Inc., New York, (1952), Third Edition, p. 246.

*Primary Examiner*—Anton H. Sutto
*Attorney, Agent, or Firm*—Robert E. Burns; Emmanuel J. Lobato; Bruce L. Adams

[57] ABSTRACT

A salt of β-diethylaminoethyl ester of p-aminobenzoic acid with the acetal of polyvinyl alcohol and glyoxalic acid which has the formula:

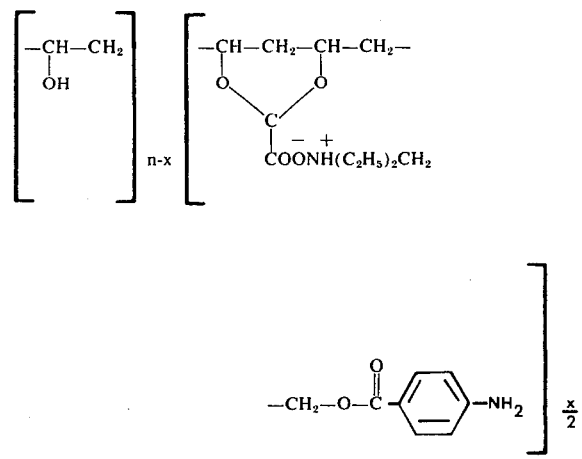

wherein $n$ is a degree of polymerization within the range of from 100 to 1,200; $x$ is a degree of substitution within the range of from 5 to 30 mol.%. The compound has local anaesthetic properties.

A method of preparing said salt of β-diethylaminoethyl ester of p-aminobenzoic acid and the acetal of polyvinyl alcohol and glyoxalic acid which comprises reacting the acetal of polyvinyl alcohol and glyoxalic acid with β-diethylaminoethyl ester of p-aminobenzoic acid in an aqueous medium, followed by isolating the desired product from the resulting solution.

6 Claims, No Drawings

SALT OF B-DIETHYLAMINOETHYL ESTER OF P-AMINOBENZOIC ACID WITH ACETAL OF POLYVINYL ALCOHOL AND GLYOXALIC AND METHOD OF PREPARING SAME

The present invention relates to a novel compound, viz. a salt of β-diethylaminoethyl ester of p-aminobenzoic acid with the acetal of polyvinyl alcohol and glyoxalic acid and to a method of preparing same.

Said novel compound according to the present invention has the formula:

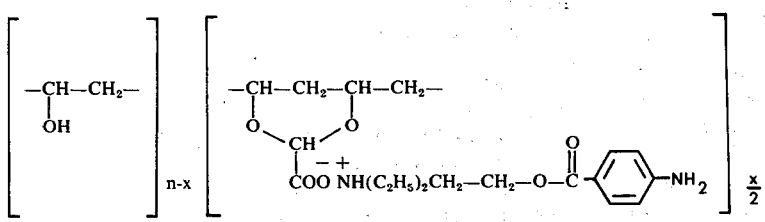

wherein $n$ is a number of units or degree of polymerization within the range of from 100 to 1,200;

$x$ is a degree of substitution within the range of from 5 to 30 molar per cent.

The compound according to the present invention comprises a white amorphous substance, well-soluble in water, insoluble in non-polar solvents and decomposing under the action of alkalis and acids.

Said salt of β-diethylaminoethyl ester of p-aminobenzoic acid with acetal of polyvinyl alcohol and glyoxalic acid features a biological activity and is useful in medicine as an active principle of a medicated compound prosessing a local anesthetic effect.

The method of preparing said salt according to the present invention comprises reacting acetal of polyvinyl alcohol and glyoxalic acid with the β-diethylaminoethyl ester of p-aminobenzoic acid in an aqueous medium, whereafter the desired product is isolated from the resulting sulution. It is preferable to effect the interaction between the acetal of polyvinyl alcohol and glyoxalic acid and the β-diethylaminoethyl ester of p-aminobenzoic acid at a temperature within the range of from 40° to 50°C. It is advisable, to obtain a good-quality product, to take the β-diathylaminoethyl ester of p-aminobenzoic acid and acetal of polyvinyl alcohol and glyoxalic acid in equimolecular amounts as calculated on carboxyl groups of the polymer and tertiary amino group of the β-diethylaminoethyl ester of p-benzoic acid. The isolation of the desired product is effected by lyophilic drzing or by precipitating the desired product from the resulting solution using acetone or ethanol.

The method of preparing a salt of the β-diethylaminoethyl ester of p-aminobenzoic acid with the acetal of polyvinyl alcohol and glyoxalic acid is performed in the following manner.

The interaction of acetal of polyvinyl alcohol and glyoxalic acid with the β-diethylaminiethyl ester of p-aminobenzoic acid is effected in an aqueous medium, where the acetal of polyvinyl alcohol and glyoxalic acid is soluble and the β-diethylaminethyl ester of p-aminobenzoic acid is insoluble.

The reaction is effected at room temperature. It is preferable to effect the reaction at a temperature within the range of from 40° to 50°C under vigorous stirring.

Upon the interaction of the acetal of polyvinyl alcohol and glyoxalic acid with the β-diethylaminoethyl ester of p-aminobenzoic acid there occurs a splitting of a hydrogen atom from the carboxyl group of the acetal of polyvinyl alcohol and glyoxalic acid which hydrogen atom accepts the undivided pair of electrons of the nitrogen atom of the β-diethylaminoethyl ester of p-aminobenzoic acid. The nitrogen-containing group becomes positively charged. The completeness of the reaction is controlled by controlling the reaction medium pH value (6.2 to 6.5). On completion of the reaction the resulting solution is filtered or centrifuged and then subjected to a lyophilic drying.

It is desirable, for the preparation of a high-quality product, that the process of reacting the acetal of polyvinyl alcohol and glyoxalic acid with the β-diethylaminoethyl ester of p-aminobenzoic acid be conducted at equimolar proportions of the reactants, as calculated on the carboxyl groups of the acetal of polyvinyl alcohol and the tertiary amino groups of of the β-diethylaminoethyl ester of p-aminobenzoic acid.

It is also possible to conduct the process of the preparation of a salt of β-diethylaminoethyl ester of p-aminobenzoic acid using an excessive amount of said ester of p-aminobenzoic acid.

In this case, on completion of the reaction, the salt of β-diethylaminoethyl ester of p-aminobenzoic acid is precipitated by means of acetone or ethanol taken in a 8-10-fold excess in respect of the starting solution volume.

The yield of the desired product is within the range of 68.0 to 98.6% by weight.

For better understanding of the present invention some examples illustrating the method of preparing a salt of the β-diethylaminoethyl ester of p-aminobenzoic acid with the acetal of polyvinyl alcohol and glyoxalic acid according to the invention are given hereinbelow.

Example 1

1 g of the acetal of polyvinyl alcohol and glyoxalic acid (with a degree of substitution for acetal of 9.5 mol.%) dissolved in 24 ml of water is added with 0.345 g of β-diethylamonoethyl ester of p-aminobenzoic acid. The mixture is stirred at room temperature for 6 hours. The resulting product is precipitated and washed with acetone or ethanol. The thus-obtained product is dried in vacuum at 65°C to a constant weight. The yield of the salt of β-diethylaminoethyl ester of p-aminobenzoic acid with the acetal of polyvinyl alcohol and glyoxalic acid is 0.955 g (71.0 wt.% of the theoretical amount).

Calculated, wt.%: N 2.30; β-diethylaminoethyl ester of p-aminobenzoic acid 20.00.

Found, wt.%: N 2.07; β-diethylaminoethyl ester of p-aminobenzoic acid 18.02.

Example 2

0.558 g of β-diethylaminoethyl ester of p-aminobenzoic acid is added with 24 ml of a 4.2% aqueous solution of acetal of polyvinyl alcohol and glyoxalic acid (with a degree of substitution for acetal of 15.3 mol.%).

The mixture is stirred at the temperature of 45°C for 30 minutes at a pH=6.2 of the solution. Then the resulting solution is filtered, the polymer is precipitated and washed with acetone. The product is dried in vacuum to a constant weight. 1.1 g of the desired product (69 wt.% of the theoretical amount) is obtained.

Calculated on the formula, wt.%: N 3.23. Found, wt.%: N 2.92.

Example 3

100 ml of a 4% aqueous solution of acetal of polyvinyl alcohol and glyoxalic acid (with a degree of substitution for acetal of 15 mol.%) are added with 2.2 g of β-diethylaminoethyl ester of p-aminobenzoic acid. The mixture is stirred at 45°C for 30 minutes until a pH=6.5 is reached. The resulting solution is filtered and subjected to a lyophilic drying. The yield of the salt of β-diethylaminoethyl ester of p-aminobenzoic acid with the acetal of polyvinyl alcohol and glyoxalic acid is 4.9 g (98.6 wt.% of the theoretical amount).

Calculated, wt.%: N 3.21; β-diethylaminoethyl ester of p-aminobenzoic acid 27.1.

Found, wt.%: N 3.04; β-diethylaminoethyl ester of p-aminobenzoic acid 26.5.

What is claimed is:

1. A salt of the β-diethylaminoethyl ester of p-aminobenzoic acid with the acetal of polyvinyl alcohol and glyoxalic acid of the formula:

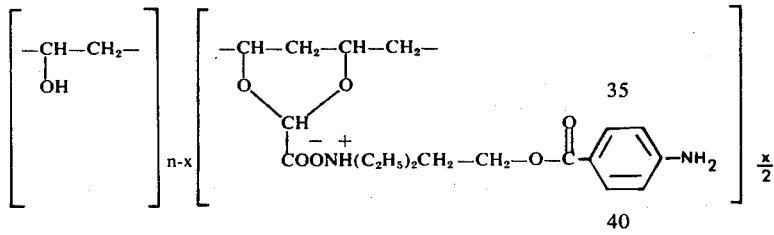

wherein $n$ is a degree of polymerization within the range of fron 100 to 1,200; $x$ is a degree of substitution within the range of from 5 to 30 mol.%.

2. A method of preparing the salt of the β-diethylaminoethyl ester of p-aminobenzoic acid with acetal of polyvinyl alcohol and glyoxalic acid as claimed in claim 1, comprising reacting the acetal of polyvinyl alcohol and glyoxalic acid with β-diethylaminoethyl ester of p-aminobenzoic acid in an aqueous medium, followed by isolation of the desired product from the resulting solution.

3. The method as claimed in claim 2, wherein the reaction between the acetal of polyvinyl alcohol and glyoxalic acid and the β-diethylaminoethyl ester of p-aminobenzoic acid is conducted at a solution pH=6.2-6.5 and a temperature within the range of from 40° to 50°C.

4. The method as claimed in claim 3, wherein the β-diethylaminoethyl ester of p-aminobenzoic acid and the acetal of polyvinyl alcohol and glyoxalic acid are taken in equimolar amounts calculated on the carboxyl groups of the polymer and the tertiary amino group of the β-diethylaminoethyl ester of p-aminobenzoic acid.

5. A method as claimed in claim 2, wherein the desired product is isolated by precipitating with a solvent selected from the group consisting of acetone and ethanol.

6. A method as claimed in claim 2, wherein the desired product is isolated by a lyophilic drying of the resulting solution.

* * * * *